United States Patent
Kong et al.

(10) Patent No.: US 10,426,439 B2
(45) Date of Patent: Oct. 1, 2019

(54) METHOD AND APPARATUS FOR OBTAINING ELASTICITY INFORMATION ABOUT REGION OF INTEREST BY USING SHEAR WAVE

(71) Applicant: Samsung Electronics Co., Ltd., Suwon-si, Gyeonggi-do (KR)

(72) Inventors: Dong-geon Kong, Hwaseong-si (KR); Jun-ho Park, Hwaseong-si (KR); Ji-young Park, Yongin-si (KR); Hyoung-ki Lee, Seongnam-si (KR); Ki-wan Choi, Anyang-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 598 days.

(21) Appl. No.: 14/293,425

(22) Filed: Jun. 2, 2014

(65) Prior Publication Data

US 2015/0164476 A1    Jun. 18, 2015

(30) Foreign Application Priority Data

Dec. 17, 2013    (KR) .................... 10-2013-0157531

(51) Int. Cl.
*A61B 8/14*    (2006.01)
*A61B 8/08*    (2006.01)
(Continued)

(52) U.S. Cl.
CPC ........... *A61B 8/485* (2013.01); *A61B 8/5207* (2013.01); *A61B 8/5223* (2013.01);
(Continued)

(58) Field of Classification Search
None
See application file for complete search history.

(56) References Cited

U.S. PATENT DOCUMENTS

| | | | | |
|---|---|---|---|---|
| 6,193,660 | B1* | 2/2001 | Jackson | A61B 8/00 600/443 |
| 6,494,834 | B2* | 12/2002 | Konofagou | A61B 8/485 600/438 |

(Continued)

FOREIGN PATENT DOCUMENTS

| | | |
|---|---|---|
| CN | 102940510 | 2/2013 |
| CN | 103300890 | 9/2013 |

(Continued)

OTHER PUBLICATIONS

Chinese Office Action dated Sep. 26, 2018 in Chinese Patent Application No. 201410790279.8.

(Continued)

*Primary Examiner* — Mark D Remaly
(74) *Attorney, Agent, or Firm* — Staas & Halsey LLP

(57) ABSTRACT

A probe irradiates an ultrasound wave to an object to induce a shear wave and first elasticity information is obtained according to a first calculating scheme. An internal region of interest of the object is set based on shear modulus values included in the first elasticity information. Second elasticity information is obtained based on the shear wave induced to the internal region of interest, according to a second calculating scheme. Accurate elasticity information is acquired by using the first and second elasticity information to obtain third elasticity information from which an elastography image is generated for display to a user.

15 Claims, 9 Drawing Sheets

(51) Int. Cl.
*G01S 7/52* (2006.01)
*G01S 15/89* (2006.01)

(52) U.S. Cl.
CPC ...... *G01S 7/52022* (2013.01); *G01S 7/52042* (2013.01); *G01S 7/52095* (2013.01); *G01S 15/8915* (2013.01); *G01S 7/52071* (2013.01)

(56) References Cited

U.S. PATENT DOCUMENTS

| | | | |
|---|---|---|---|
| 7,252,004 | B2 | 8/2007 | Fink et al. |
| 7,753,847 | B2* | 7/2010 | Greenleaf ............... A61B 8/00 600/438 |
| 8,118,744 | B2 | 2/2012 | Palmeri et al. |
| 9,370,339 | B2 | 6/2016 | Hazard et al. |
| 2011/0028838 | A1* | 2/2011 | Pernot ................ A61B 5/0048 600/437 |
| 2012/0136250 | A1* | 5/2012 | Tabaru ..................... A61B 8/08 600/438 |
| 2012/0253194 | A1* | 10/2012 | Tamura ................. A61B 8/485 600/438 |
| 2013/0096430 | A1* | 4/2013 | Yoshiara ............. A61B 8/0841 600/438 |
| 2013/0245442 | A1* | 9/2013 | Hazard ............... G01S 7/52036 600/438 |
| 2013/0296698 | A1 | 11/2013 | Fraser et al. |
| 2013/0317361 | A1* | 11/2013 | Tabaru ..................... A61B 8/42 600/438 |
| 2014/0081136 | A1* | 3/2014 | Zhao ................... A61B 8/5223 600/438 |
| 2014/0094702 | A1* | 4/2014 | Kim .................. G01N 29/0654 600/438 |
| 2015/0148676 | A1* | 5/2015 | Choi .................... A61B 8/468 600/438 |
| 2016/0183926 | A1* | 6/2016 | Asami .................. A61B 8/485 600/438 |

FOREIGN PATENT DOCUMENTS

| | | |
|---|---|---|
| CN | 103347450 | 10/2013 |
| KR | 10-1306491 | 9/2013 |

OTHER PUBLICATIONS

Chinese Office Action dated May 21, 2019 in Chinese Patent Application No. 201410790279.8.

* cited by examiner

FIG. 8

| ROI | Elasticity 1 | Elasticity 2 |
|---|---|---|
| #1 | Mean 40kPa<br>Std 3kPa | Mean 44kPa<br>Std 2kPa |
| #2 | Mean 60kPa<br>Std 5kPa | Mean 58kPa<br>Std 6kPa |
| #3 | Mean 35kPa<br>Std 2kPa | Mean 38kPa<br>Std 3kPa |

(a)

| ROI | Elasticity |
|---|---|
| #1 | Mean 42.7kPa<br>Std 1.66kPa |
| #2 | Mean 59.2kPa<br>Std 3.84kPa |
| #3 | Mean 35.9kPa<br>Std 1.66kPa |

(b)

ism METHOD AND APPARATUS FOR OBTAINING ELASTICITY INFORMATION ABOUT REGION OF INTEREST BY USING SHEAR WAVE

CROSS-REFERENCE TO RELATED APPLICATIONS

This application claims the benefit of Korean Patent Application No. 10-2013-0157531, filed on Dec. 17, 2013, in the Korean Intellectual Property Office, the disclosure of which is incorporated herein in its entirety by reference.

BACKGROUND

1. Field

One or more embodiments disclosed herein relate to a method and apparatus for obtaining elasticity information about a region of interest (ROI) by using a shear wave.

2. Description of the Related Art

A computer-aided diagnosis (CAD) system, which primarily analyzes a medical image such as an ultrasound image, a magnetic resonance (MR) image, or a computed tomography (CT) image to provide the presence and position of abnormal tissue to a user, has been recently developed. The CAD system refers to a system that determines the presence, size, and position of an abnormal tissue in a medical image by using a computer to detect the abnormal tissue, and provides the detection result to a user, thereby aiding an image diagnosis of the user. The CAD system may be used in combination with a medical apparatus such as an ultrasound apparatus, a magnetic resonance imaging (MRI) apparatus, a CT apparatus, or the like.

SUMMARY

One or more embodiments disclosed herein include a method and apparatus for obtaining elasticity information about an ROI by using a shear wave.

One or more embodiments disclosed herein include a non-transitory computer-readable storage medium which stores a program for executing the method in a computer.

Additional aspects will be set forth in part in the description which follows and, in part, will be apparent from the description, or may be learned by practice of the disclosed embodiments.

According to one or more embodiments disclosed herein, a method of obtaining elasticity information of a region of interest (ROI) includes: obtaining first elasticity information of an object by using a shear wave induced to the object, setting an internal ROI of the object, based on the first elasticity information, obtaining second elasticity information of the ROI by using a shear wave induced to the ROI, and obtaining third elasticity information of the ROI by using the first and second elasticity information.

The obtaining of first elasticity information may include: receiving an echo signal of a plane ultrasound wave which is irradiated onto the object, performing beamforming of the echo signal, and calculating a displacement of the shear wave induced to the object by using the beamformed signal, and determining a velocity of the shear wave induced to the object by using the calculated displacement. The plane ultrasound wave may include an ultrasound wave that does not form a focal point in a region corresponding to the object.

The determining of the velocity of the first wave may include determining the velocity of the shear wave induced to the object by using a wave equation, including the displacement, or by using a change amount of the displacement based on time.

The obtaining of second elasticity information may include: receiving an echo signal of an ultrasound wave which is irradiated onto the ROI, performing beamforming of the echo signal to form at least one or more scan lines, and calculating a displacement of the shear wave induced to the ROI by using the beamformed signal, and determining a velocity of the shear wave induced to the ROI by using the calculated displacement. The ultrasound wave irradiated onto the ROI may include an ultrasound wave that forms a focal point at a portion of the ROI.

The determining of the velocity of the shear wave may include determining the velocity of the shear wave induced to the ROI by using a wave equation, including the displacement, or by using a change amount of the displacement based on time.

The obtaining of third elasticity information may include obtaining the third elasticity information by using a velocity of a first shear wave and a standard deviation of the velocity in the ROI among a plurality of elasticity values included in the first elasticity information and a velocity of a second shear wave and a standard deviation of the velocity in the ROI among a plurality of elasticity values included in the second elasticity values.

The method may further include calculating confidence scores of elasticity values included in the first elasticity information and confidence scores of elasticity values included in the second elasticity information.

The method may further include generating an elastography image indicating the ROI, based on the third elasticity information.

According to one or more embodiments, provided is a non-transitory computer-readable storage medium which stores one or more programs for executing any one of the methods of obtaining elasticity information disclosed herein.

According to one or more embodiments disclosed herein, an apparatus for obtaining elasticity information of an ROI includes: a first obtainment unit configured to (suitable for, capable of, arranged to, adapted to, etc.) obtain first elasticity information of an object by using a shear wave induced to the object, a setting unit configured to (suitable for, capable of, arranged to, adapted to, etc.) set an internal ROI of the object, based on the first elasticity information, a second obtainment unit configured to (suitable for, capable of, arranged to, adapted to, etc.) obtain second elasticity information of the ROI by using a shear wave induced to the ROI, and a third obtainment unit configured to (suitable for, capable of, arranged to, adapted to, etc.) obtain third elasticity information of the ROI by using the first and second elasticity information.

The apparatus may include a beamforming unit to perform beamforming for an echo signal of a plane ultrasound wave which is irradiated onto the object, wherein the first obtainment unit calculates a displacement of the shear wave induced to the object by using the beamformed signal, and determines a velocity of the shear wave induced to the object by using the calculated displacement. The plane ultrasound wave may include an ultrasound wave that does not form a focal point in a region corresponding to the object.

The apparatus may include a beamforming unit to perform beamforming for an echo signal of an ultrasound wave, which is irradiated onto the ROI, to form at least one or more scan lines, wherein the second obtainment unit calculates a displacement of the shear wave induced to the ROI by using the beamformed signal, and determines a velocity of the shear wave induced to the ROI by using the calculated displacement. The ultrasound wave irradiated onto the ROI may include an ultrasound wave that forms a focal point at a portion of the ROI.

The third obtainment unit may obtain the third elasticity information by using a velocity of a first shear wave and a standard deviation of the velocity in the ROI among a plurality of elasticity values included in the first elasticity information and a velocity of a second shear wave and a standard deviation of the velocity in the ROI among a plurality of elasticity values included in the second elasticity values.

The apparatus may further include a confidence score calculating unit to calculate confidence scores of elasticity values included in the first elasticity information and confidence scores of elasticity values included in the second elasticity information.

The apparatus may further include an image generating unit to generate an elastography image indicating the ROI, based on the third elasticity information.

According to one or more embodiments disclosed herein, a method of obtaining elasticity information of a region of interest (ROI) in an object includes: irradiating a first pushing beam to induce a first shear wave in the object, irradiating a first plane wave and receiving a first echo signal which includes information on displacement of the first shear wave, to obtain first elasticity information about the object, setting an internal ROI of the object, based on the first elasticity information, irradiating a second pushing beam to induce a second shear wave in the ROI, irradiating a second plane wave that forms a focal point in a first portion of the ROI, and receiving a second echo signal which includes information on displacement of the second shear wave, to obtain second elasticity information about the ROI, and obtaining third elasticity information about the ROI based on the first and second elasticity information.

The method may further include irradiating a third pushing beam to induce a third shear wave in the ROI, and irradiating a third plane wave that forms a focal point in a second portion of the ROI, and receiving a third echo signal, wherein the second echo signal and third echo signal are used to obtain an echo signal for the whole ROI.

The setting the internal ROI of the object based on the first elasticity information may further include setting the internal ROI of the object in a region corresponding to the object where the first elasticity information is greater than a predetermined threshold value.

The first elasticity information may include a value representing a shear modulus value, the predetermined threshold value may correspond to a predetermined shear modulus value, and when a shear modulus value in a region of the object is greater than the predetermined shear modulus value, the region may be set as an internal ROI of the object.

The method may further include generating an elastography image of the object based on the first elasticity information, where the elastography image may include different brightness values. The predetermined threshold value may correspond to a predetermined brightness value, and when a brightness value in a region of the object is greater than the predetermined brightness value, the region may be set as an internal ROI of the object.

The setting the internal ROI of the object based on the first elasticity information may further include receiving a user input setting the internal ROI of the object.

The obtaining third elasticity information may further include calculating a velocity in the ROI using the sum of a first weight applied to a velocity of the first shear wave, and a second weight applied to a velocity of the second shear wave, and calculating a standard deviation of the velocity in the ROI based on at least one of a standard deviation of the velocity of the first shear wave, and a standard deviation of the velocity of the second shear wave.

BRIEF DESCRIPTION OF THE DRAWINGS

These and/or other aspects will become apparent and more readily appreciated from the following description of the embodiments, taken in conjunction with the accompanying drawings in which:

FIG. 8 includes diagrams for describing an example in which an image display apparatus according to an embodiment displays first to third elasticity information;

DETAILED DESCRIPTION

Figure 1:
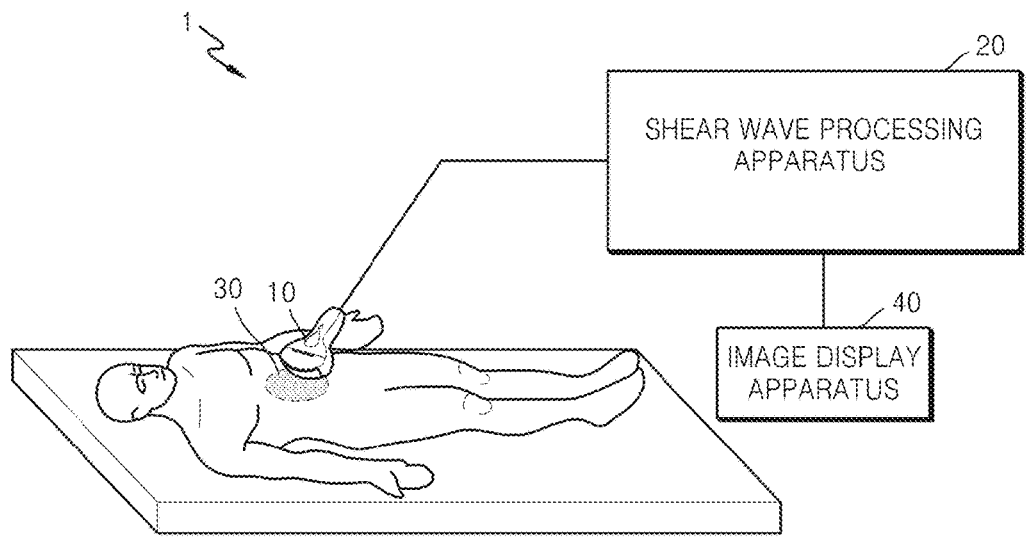
FIG. 1 is a diagram of an elasticity analysis system according to an embodiment.

Reference will now be made in detail to embodiments, examples of which are illustrated in the accompanying drawings, wherein like reference numerals refer to like elements throughout. In this regard, the disclosed embodiments may have different forms and should not be construed as being limited to the descriptions set forth herein. Accordingly, the embodiments are merely described below, by referring to the figures, to explain aspects of the disclosure. As used herein, the term "and/or" includes any and all combinations of one or more of the associated listed items. Expressions such as "at least one of," when preceding a list of elements, modify the entire list of elements and do not modify the individual elements of the list.

FIG. 1 is a diagram of an elasticity analysis system 1 according to an embodiment.

Referring to FIG. 1, the elasticity analysis system 1 may include a probe 10, a shear wave processing apparatus 20, and an image display apparatus 40.

The elasticity analysis system 1 of FIG. 1 is illustrated as including various elements which may be associated with the elasticity analysis system 1. However, it will be understood by those of ordinary skill in the art that the elasticity analysis system 1 may further include general-use elements in addition to the elements shown in FIG. 1.

Ultrasound elastography technology analyzes an elasticity of tissue to determine a stiffness difference between normal tissue and abnormal tissue, thereby performing a diagnosis.

For example, the elasticity analysis system 1 according to an embodiment may analyze an elasticity of tissue by using an ultrasound wave to determine whether there is a cancer or a tumor, or by using high intensity focused ultrasound (HIFU), when treating tissue, the elasticity analysis system 1 may determine a state of internal tissue of a human body as to whether the treatment is completed.

The probe 10 may irradiate an ultrasound wave onto an object 30 to receive an echo signal. Here, the object 30 denotes a peripheral region including an ROI. For example, the object 30 may denote a certain region of a body of a patient which is diagnosed, but is not limited thereto. Also, the ultrasound wave irradiated from the probe 10 may be an ultrasound wave used to induce a shear wave, or may be an ultrasound wave used to obtain elasticity information about the object 30.

For example, the probe 10 may irradiate an ultrasound wave (e.g., a pushing beam) used to induce a shear wave to the object 30 based on a control signal of the shear wave processing apparatus 20. Also, the probe 10 may irradiate an ultrasound wave used to obtain elasticity information about the object 30 based on the control signal of the shear wave processing apparatus 20, and may receive an echo signal of the irradiated ultrasound wave. The probe 10 may transmit the received echo signal to the shear wave processing apparatus 20. Here, the ultrasound wave used to obtain the elasticity information about the object 30 may denote an ultrasound wave (for example, a plane wave), which does not form a focal point in a region corresponding to the object 30. Alternatively, the ultrasound wave used to obtain the elasticity information about the object 30 may denote an ultrasound wave (for example, a focused wave) that forms the focal point at a portion of the region corresponding to the object 30.

The probe 10 may include a one-dimensional (1D) array or a two-dimensional (2D) array of a plurality of transducers. Here, each of the transducers may irradiate an ultrasound wave or receive an echo signal based on the control signal of the shear wave processing apparatus 20. That is, some or all of the transducers included on the probe may irradiate an ultrasound wave and/or receive the echo signal.

The image display apparatus 40 may display an ultrasound image generated by the shear wave processing apparatus 20. For example, the image display apparatus 40 may include all output apparatuses such as a display panel, a mouse, a liquid crystal display (LCD) screen, a monitor, etc. which are provided in the elasticity analysis system 1. The image display apparatus 40 may also include, for example, a light emitting diode (LED) display, organic light emitting diode (OLED) display, plasma display panel (PDP), cathode ray tube (CRT), and the like. Elasticity information obtained through analysis by the shear wave processing apparatus 20 may be provided to a user through the image display apparatus 40, and used to determine a state or a characteristic change of tissue.

The shear wave processing apparatus 20 may control an operation of the probe 10, and obtain elasticity information about the object 30 or an ROI of the object 30 by using the echo signal received by the probe 10. Here, the elasticity information may include a value representing a strain, stiffness, Young's modulus, and/or shear modulus of each of the tissues composing the object 30 or the ROI.

The shear wave processing apparatus 20 according to an embodiment of the disclosure may obtain first elasticity information by using a shear wave induced to the object 30, and may set an internal ROI of the object 30 based on the obtained first elasticity information. The shear wave processing apparatus 20 may obtain second elasticity information by using a shear wave induced to the ROI. The shear wave processing apparatus 20 may obtain third elasticity information by using the first and second elasticity information. Here, the first elasticity information denotes elasticity information about tissues composing the object 30, and each of the second and third elasticity information denotes elasticity information about tissues composing the ROI. For example, the ROI may refer to an area of tissues which is smaller in size than a size of tissues composing the object 30.

As described above, the shear wave processing apparatus 20 may obtain the third elasticity information by using the first and second elasticity information which are obtained by using different processes, and thus the shear wave processing apparatus 20 may accurately obtain elasticity information (for example, an elasticity value and/or an elastography image) about the tissues composing the ROI.

Hereinafter, an example of operating the shear wave processing apparatus 20 will be described in detail with reference to FIGS. 2 to 10.

Figure 2:
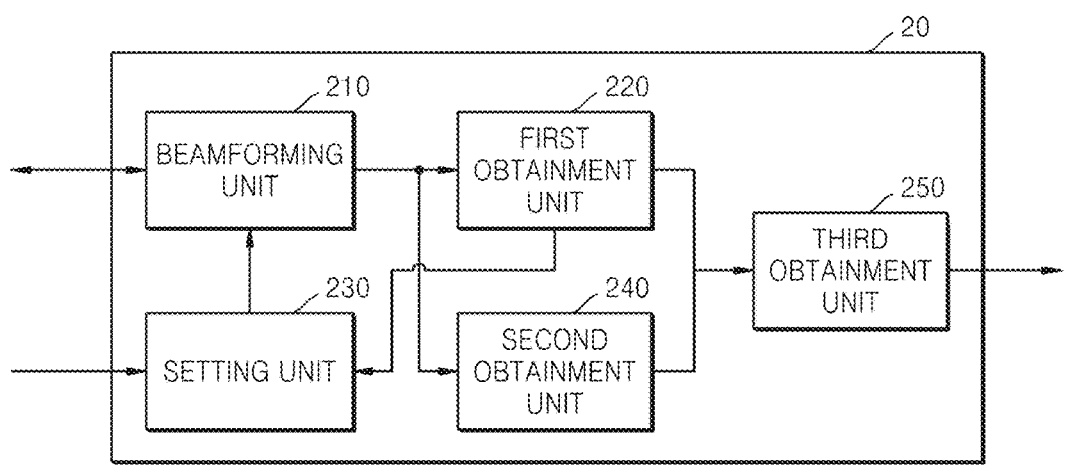
FIG. 2 is a block diagram of a shear wave processing apparatus according to an embodiment.

FIG. 2 is a block diagram of a shear wave processing apparatus 20 according to an embodiment.

Referring to FIG. 2, the shear wave processing apparatus 20 may include a beamforming unit 210, a first obtainment unit 220, a setting unit 230, a second obtainment unit 240, and a third obtainment unit 250.

The shear wave processing apparatus 20 of FIG. 2 is illustrated as including various elements which may be associated with the shear wave processing apparatus 20. However, it will be understood by those of ordinary skill in the art that the shear wave processing apparatus 20 may further include general-use elements in addition to the elements of FIG. 2.

Moreover, the beamforming unit 210, the first obtainment unit 220, the setting unit 230, the second obtainment unit 240, and the third obtainment unit 250 of the shear wave processing apparatus 20 of FIG. 2 may each correspond to one or more processors. Alternatively, one or more processors may correspond to one or more of the beamforming unit 210, the first obtainment unit 220, the setting unit 230, the second obtainment unit 240, and the third obtainment unit 250 of the shear wave processing apparatus 20 of FIG. 2. Each of the processors may be implemented as an array of a plurality of logic gates, or may be implemented as a combination of a general-use microprocessor and a memory that stores a program executable by the microprocessor. As another example, a processing device may be implemented using one or more general-purpose and/or special purpose computers, such as, for example, a processor, an image processor, a controller and an arithmetic logic unit, a central processing unit (CPU), a graphics processing unit (GPU), a digital signal processor (DSP), a microcomputer, a field programmable array, a programmable logic unit, an application-specific integrated circuit (ASIC), a microprocessor or any other device capable of responding to and executing instructions in a defined manner. Also, it will be understood by those of ordinary skill in the art that the elements may be implemented as another type of hardware.

The beamforming unit 210 may perform transmission beamforming for the ultrasound wave irradiated from the probe 10, and/or may perform reception beamforming for the echo signal received by the probe 10.

The transmission beamforming may include an operation of controlling an amplitude or phase of an ultrasound wave irradiated from each of the transducers configuring the probe 10. Also, the transmission beamforming may include an operation of determining at least one or more transducers, intending to irradiate an ultrasound wave, from among the plurality of transducers configuring the probe 10. That is, the transmission beamforming may determine at least one or more transducers which may be used to irradiate an ultrasound wave, from among the plurality of transducers configuring the probe 10.

For example, by assuming that the probe 10 irradiates an ultrasound wave used to induce a shear wave to the object 30, the beamforming unit 210 may determine a transducer intending to irradiate an ultrasound wave among the plurality of transducers configuring the probe 10, and/or may determine an amplitude and phase of an ultrasound wave which is to be irradiated from each transducer, thereby transmitting the determined information to the probe 10.

As another example, by assuming that the probe 10 irradiates an ultrasound wave (which is used to obtain elasticity information) to the object 30, the beamforming unit 210 may determine a transducer intending to irradiate an ultrasound wave among the plurality of transducers configuring the probe 10, and/or may determine an amplitude and phase of an ultrasound wave which is to be irradiated from each transducer, thereby transmitting the determined information to the probe 10.

The reception beamforming may include an operation of processing the echo signal received by the probe 10. For example, the beamforming unit 210 may analog-digital convert the received echo signal to generate a digital signal. The beamforming unit 210 may perform the reception beamforming for the digital signal to generate a reception focusing signal, and may generate ultrasound data by using the reception focusing signal. Here, the ultrasound data may include a radio frequency (RF) signal, but is not limited thereto.

The beamforming unit 210 may perform beamforming for the echo signal in order for at least one or more scan lines to be formed, to obtain the second elasticity information. A detailed method in which the beamforming unit 210 operates will be described below with reference to FIG. 3.

The first obtainment unit 220 may obtain the first elasticity information of the object 30 by using the shear wave induced to the object 30. In other words, the first obtainment unit 220 may obtain the first elasticity information of the object 30 based on information indicating propagation of the shear wave induced to the object 30. Here, the object 30 may denote a region including an ROI and a peripheral region thereof, and the ROI may denote a lesion.

The setting unit 230 may set an internal ROI of the object 30 based on the first elasticity information. For example, the setting unit 230 may set the ROI in a region corresponding to the object 30 according to whether the first elasticity information exceeds a predetermined threshold value. Alternatively, or additionally, the setting unit 230 may set a region, which is set by a user, to the ROI based on the first elasticity information. Here, the region set by the user may be transmitted as an external signal to the setting unit 230.

The second obtainment unit 240 may obtain the second elasticity information of the ROI by using the shear wave induced to the ROI. That is, after the ROI is set, the second obtainment unit 240 may obtain the second elasticity information of the ROI based on information indicating propagation of the shear wave induced to the ROI.

The third obtainment unit 250 may obtain the third elasticity information of the ROI by using the first and second elasticity information. For example, the third obtainment unit 250 may combine the first and second elasticity information respectively transmitted from the first and second obtainment units 220 and 240 to obtain the third elasticity information. In other words, the third obtainment unit 250 may combine the first and second elasticity information, and thus accurately obtain elasticity information about tissues composing the ROI. For example, a first weight may be applied to the first elasticity information and a second weight may be applied to the second elasticity information, and the third elasticity information may correspond to a combination of the weighted first elasticity information and the weighted second elasticity information.

Hereinafter, a detailed operation performed by each of the elements included in the shear wave processing apparatus 20 will now be described with reference to FIG. 3.

Figure 3:
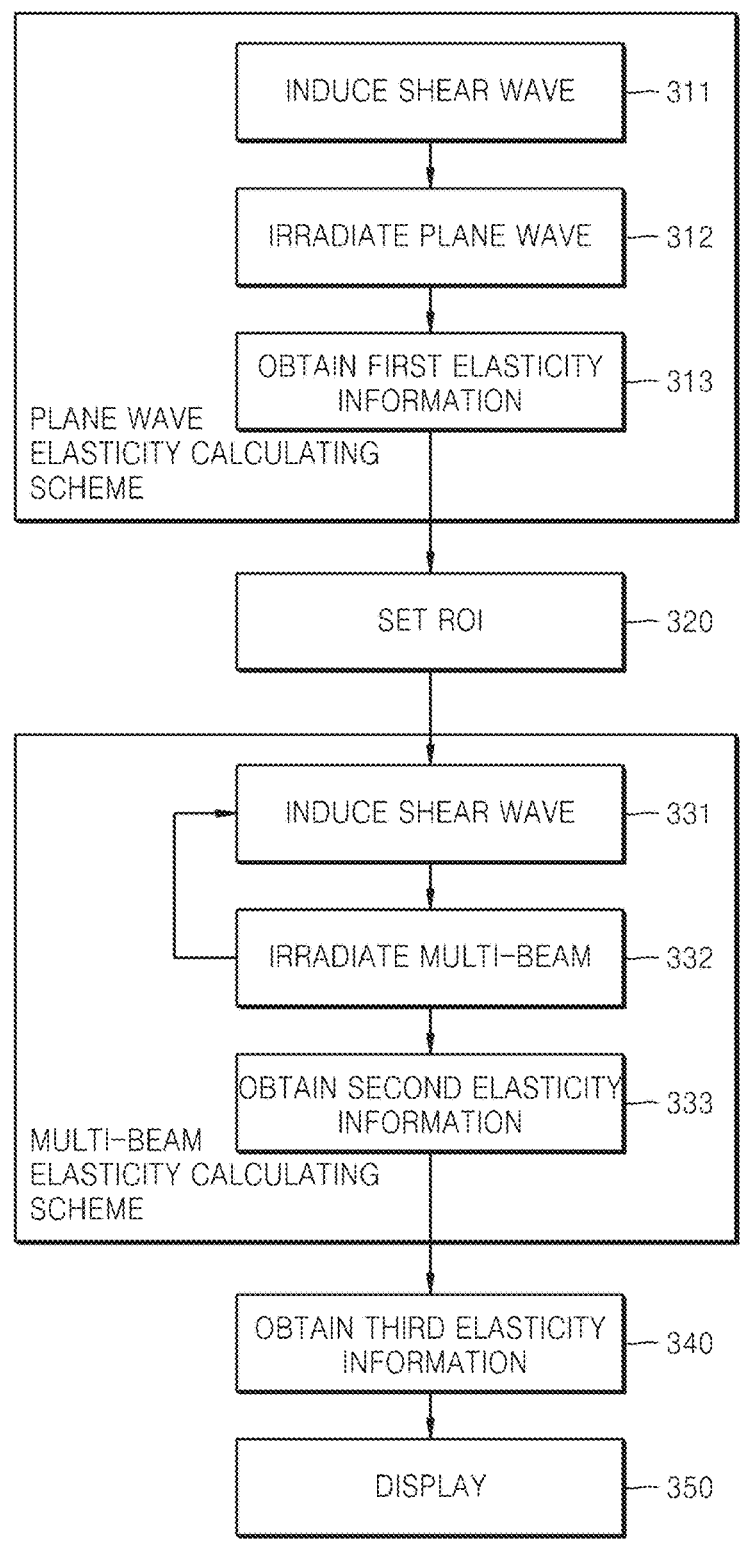
FIG. 3 is a flowchart of an operation performed by the elasticity analysis system according to an embodiment.

FIG. 3 is a flowchart for describing an example of an operation performed by the elasticity analysis system 1, according to an embodiment.

Operations 311 to 313 indicate operations which may be performed by the probe 10, the beamforming unit 210, and the first obtainment unit 220 until the first obtainment unit 220 obtains the first elasticity information. Here, the first elasticity information may be obtained by a plane wave elasticity calculating scheme.

In operation 311, the probe 10 irradiates an ultrasound wave used to induce a shear wave to the object 30. In detail, the beamforming unit 210 performs the transmission beamforming to transmit a control signal to the probe 10. Then, the probe 10 irradiates the ultrasound wave used to induce the shear wave to the object 30 based on the control signal transmitted from the beamforming unit 210.

In operation 312, the probe 10 irradiates an ultrasound wave, used to obtain elasticity information, to the object 30 to receive an echo signal. Here, the ultrasound wave used to obtain the elasticity information may be a plane wave. The echo signal, which is received by the probe 10 in operation 312, may include information about the shear wave (which is induced in operation 311) being propagated through the object 30.

Hereinafter, operations 311 and 312 will be described in detail with reference to FIG. 4.

Figure 4:
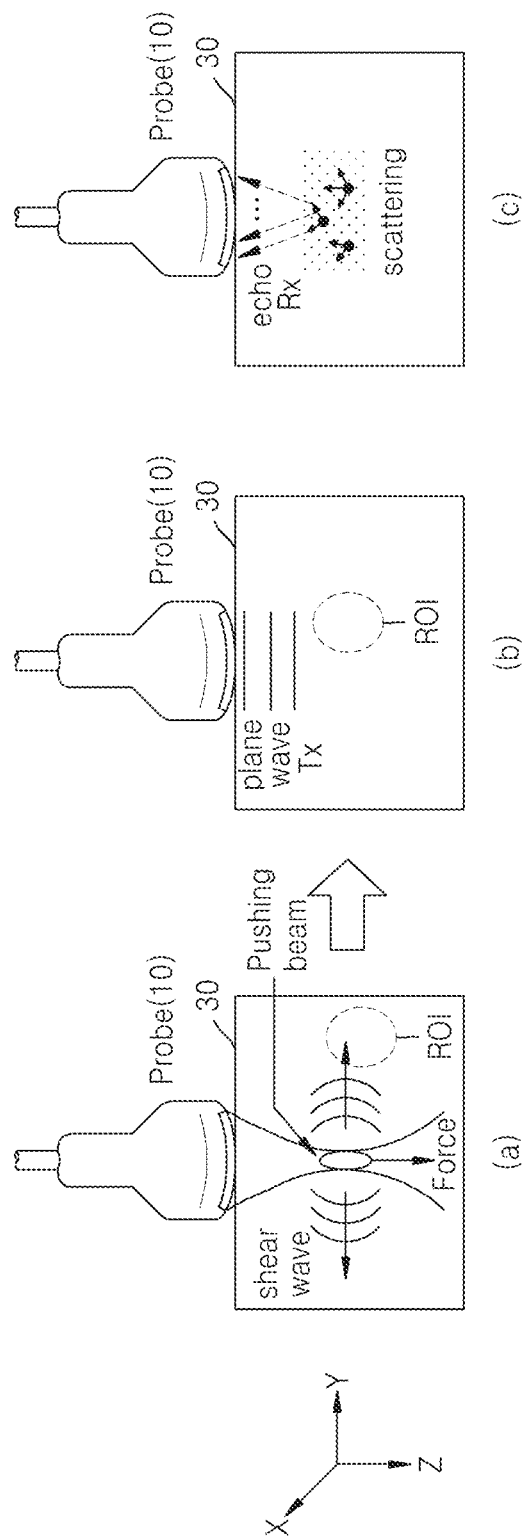
FIG. 4 includes diagrams for describing operations 311 and 312 of FIG. 3 according to an embodiment.

FIG. 4 includes diagrams for describing operations 311 and 312 of FIG. 3 according to an embodiment. In detail, FIG. 4 (a) is a diagram for describing operation 311 of FIG. 3, and FIGS. 4 (b) and (c) are diagrams for describing operation 312 of FIG. 3.

Referring to FIG. 4 (a), the probe 10 irradiates an ultrasound wave (hereinafter referred to as a pushing beam) that forms a focal point at an internal certain position of the object 30 (e.g., a predefined or predetermined area or point internal to the object 30), based on the control signal transmitted from the beamforming unit 210. For example, the probe 10 may irradiate an acoustic radiation force impulse (ARFI) onto the internal certain position of the object 30. A shear wave induced to the object 30 may be generated from the irradiated ARFI, and thus, a displacement of tissue configuring the object 30 may be generated.

When a force of the pushing beam is applied in a Z-axis direction, a P wave (a plane wave), an S wave (a shear wave), and a PS wave (which is generated by coupling the P wave and the S wave) are generated. Here, the shear wave denotes the S wave that vibrates in a wave traveling direction from a vibration source to which the force is applied, and travels in a Y-axis direction (e.g., in the positive and/or negative Y-direction).

In an example embodiment, an ultrasound wave signal transmitted from the probe 10 may be described as being used as the force of the pushing beam which is used to generate a shear wave. However, a vibrator of an MRI apparatus or an ultrasound apparatus for treatment, such as a HIFU apparatus which is provided outside the elasticity analysis system 1 so as to generate a shear wave, may also be used. That is, it may be understood by one of ordinary skill in the art that a device or apparatus for generating a shear wave may be variously implemented without being limited to an arbitrary apparatus.

Referring to FIG. 4 (*b*), the probe 10 irradiates an ultrasound wave used to obtain the elasticity information of the object 30, based on the control signal transmitted from the beamforming unit 210. Here, the ultrasound wave irradiated from the probe 10 may be a plane wave. In other words, the probe 10 may irradiate the ultrasound wave that does not form a focal point in a region corresponding to the object 30. For example, the probe 10 may irradiate the plane wave at a velocity of about 1,000 frames/s to about 10,000 frames/s, but is not limited thereto.

Referring to FIG. 4 (*c*), the probe 10 receives an echo signal of the plane wave. In other words, the probe 10 receives the echo signal which is generated according to the plane wave (irradiated from the probe 10) being reflected by the tissues composing the object 30.

When the plane wave is irradiated from each of the transducers included in the probe 10, the plane wave is partially reflected from layers between the tissues. For example, the plane wave may be reflected from parts (for example, internal blood cells of blood plasma and internal small tissues of organs) in which a density changes inside the object 30. A plurality of reflected echo signals vibrate the transducers, which respectively output electrical pulses based on the vibrations.

Referring again to FIG. 3, in operation 313, the first obtainment unit 220 obtains the first elasticity information. For example, the beamforming unit 210 performs the reception beamforming for the echo signal received by the probe 10, and transmits the beamformed signal to the first obtainment unit 220. The first obtainment unit 220 calculates a displacement of a shear wave by using the beamformed signal. The first obtainment unit 220 determines the first elasticity information by using the calculated displacement.

For example, the first obtainment unit 220 may determine a velocity of the shear wave inside the object 30, based on the calculated displacement. In this case, the first obtainment unit 220 may determine the velocity of the shear wave by using a wave equation, including the displacement of the shear wave as a variable, or an amount of change of the displacement of the shear wave based on time.

As an example, the first obtainment unit 220 may determine the velocity of the shear wave by using the following wave equation (Equation (1)):

$$\frac{\partial^2 u}{\partial t^2} = C_s^2 \cdot \left( \frac{\partial^2 u}{\partial x^2} + \frac{\partial^2 u}{\partial y^2} + \frac{\partial^2 u}{\partial z^2} \right) \quad (1)$$

where u denotes a displacement of a shear wave and Cs denotes a velocity of the shear wave.

As another example, the first obtainment unit 220 may determine the velocity of the shear wave by using the amount of change of the displacement of the shear wave based on time. For example, by assuming that t1 is a time taken until the shear wave reaches a first position "x1" of the object 30 and t2 is a time taken until the shear wave reaches a second position "x2" of the object 30, the first obtainment unit 220 may determine the velocity "v" of the shear wave by using the following Equation (2):

$$v = \frac{x_2 - x_1}{t_2 - t_1} \quad (2)$$

The first obtainment unit 220 may determine the first elasticity information by using the determined velocity.

The plane wave elasticity calculating scheme described above with reference to operations 311 to 313 may obtain elasticity information about a wide region of the object 30, but may be reduced in accuracy. In other words, the first obtainment unit 220 may obtain elasticity information of a wide region by using an echo signal of a plane wave which is irradiated once, but may be low in accuracy of the elasticity information.

The shear wave processing apparatus 20 according to an embodiment of the disclosure may set an internal ROI of the object 30 based on the first elasticity information, and may obtain the second elasticity information about the ROI. The shear wave processing apparatus 20 may obtain the third elasticity information about the ROI by using the first and second elasticity information. Therefore, the shear wave processing apparatus 20 accurately obtains elasticity information about the ROI.

In operation 320, the setting unit 230 sets the ROI of the object 30 based on the first elasticity information. Hereinafter, an operation of the setting unit 230 will be described in detail with reference to FIG. 5.

Figure 5:
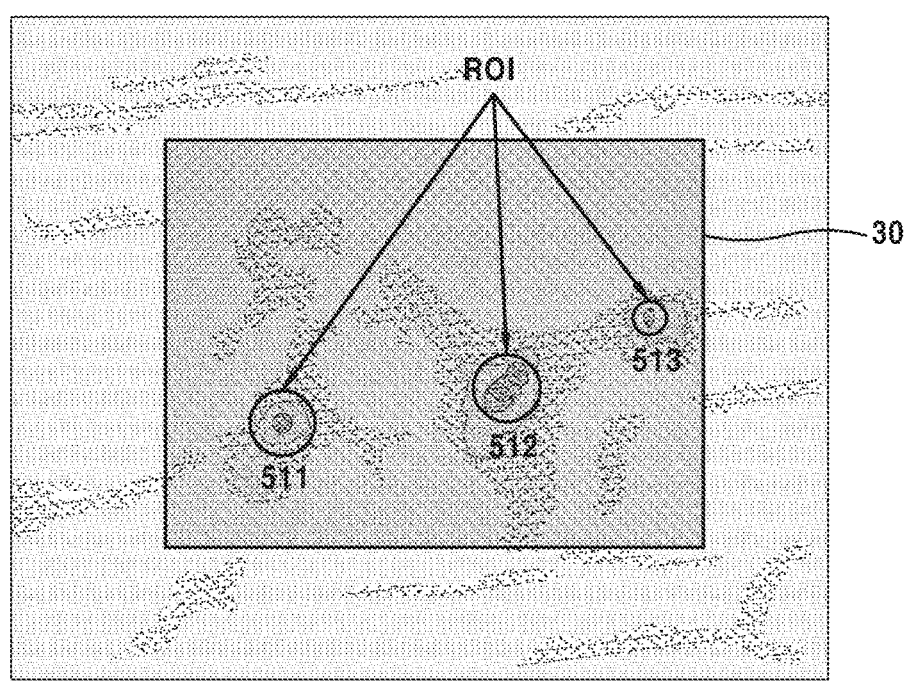
FIG. 5 is a diagram of an ROI according to an embodiment.

FIG. 5 is a diagram of an ROI according to an embodiment.

FIG. 5 shows an elastography image of the object 30, which is generated based on the first elasticity information. Referring to FIG. 5, an example of each of ROIs 511 to 513 included in the object 30 is illustrated. In FIG. 5, it is illustrated that a total of three ROIs 511 to 513 are included in the object 30, but the disclosure is not limited thereto. For example, there may be one ROI, two ROIs, or more than three ROIs included in the object 30.

When the first elasticity information is assumed as a shear modulus of the object 30, the elastography image of FIG. 5 may be an image in which a displacement of a shear wave, which is changed with time, is expressed as a color difference, or may be an image in which the displacement of the shear wave is expressed as a brightness difference.

Generally, a stiffness difference occurs between abnormal tissue and normal tissue, and the abnormal tissue may be determined by analyzing the stiffness difference. For example, abnormal tissue such as a cancer or a tumor may have higher elasticity than that of normal tissue. For this reason, the abnormal tissue such as a cancer or a tumor has a higher shear modulus than that of peripheral normal tissue. Also, even when necrotizing tissue by using an ultrasound wave for treatment such as through HIFU, elasticity increases as the necrosis of the tissue progresses.

Therefore, the setting unit 230 sets regions, in which a shear modulus has a predetermined threshold value or more in the object 30, to the ROIs 511 to 513. For example, when the first obtainment unit 220 obtains the shear modulus as a numerical value, the setting unit 230 may set regions, which indicate a numerical value that is equal to or more than the threshold value, to the ROIs 511 to 513. Also, when the first obtainment unit 220 generates an elastography image by using the shear modulus, the setting unit 230 may set regions, which indicate a brightness equal to or more than the threshold value or indicates a certain color, to the ROIs 511 to 513.

Additionally, or alternatively, the setting unit 230 may set a region, which is set by a user based on the first elasticity information, to an ROI. Here, the region set by the user may be transmitted as an external signal to the setting unit 230.

Referring again to FIG. 3, operations 331 to 333 indicate operations which may be performed by the probe 10, the beamforming unit 210, and the second obtainment unit 220 until the second obtainment unit 220 obtains the second elasticity information. Here, the second elasticity information may be obtained by a multi-beam shear modulus calculating scheme.

In operation 331, the probe 10 irradiates an ultrasound wave used to induce a shear wave to an ROI. In operation 332, the probe 10 irradiates an ultrasound wave, used to obtain elasticity information, to the ROI to receive an echo signal. The echo signal, which is received by the probe 10 in operation 332, may include information about the shear wave (which is induced in operation 331) being propagated through the ROI.

As described above with reference to operation 312, the probe 10 irradiates a plane wave onto the object 30. On the other hand, in operation 332, the probe 10 irradiates an ultrasound wave that forms a focal point at a portion of the ROI.

Hereinafter, operations 331 and 332 will be described in detail with reference to FIG. 6.

Figure 6:
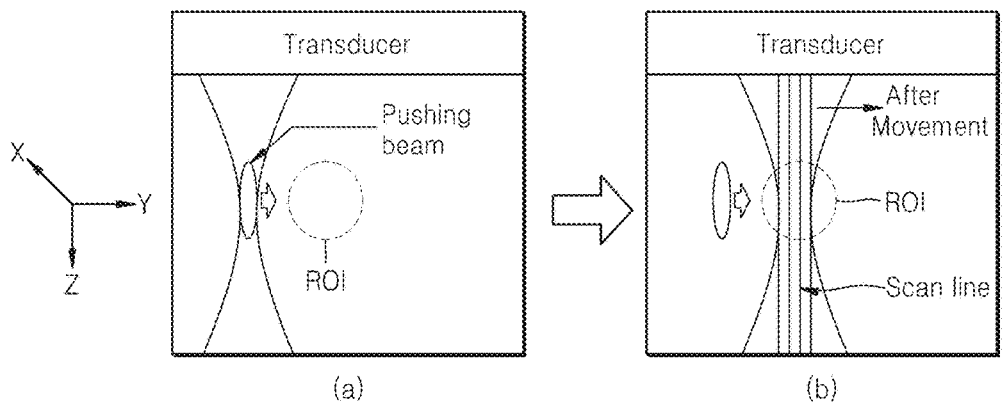
FIG. 6 includes diagrams for describing operations 331 and 332 of FIG. 3 according to an embodiment.

FIG. 6 includes diagrams for describing operations 331 and 332 of FIG. 3 according to an embodiment. In detail, FIG. 6 (*a*) is a diagram for describing operation 331 of FIG. 3, and FIG. 6(*b*) is a diagram for describing operation 332 of FIG. 3.

Referring to FIG. 6 (*a*), the probe 10 irradiates a pushing beam that forms a focal point at a certain position near an ROI, based on the control signal transmitted from the beamforming unit 210. A method, in which the probe 10 irradiates the pushing beam to induce a shear wave to the ROI, is as described above with reference to FIG. 4 (*a*).

Referring to FIG. 6 (*b*), the probe 10 irradiates an ultrasound wave used to obtain elasticity information of the ROI, based on the control signal transmitted from the beamforming unit 210. Here, the ultrasound wave irradiated from the probe 10 may be a plane wave that forms a focal point in a portion of the ROI.

The beamforming unit 210 performs beamforming for a received echo signal in order for at least one or more scan lines to be formed. In other words, the ultrasound wave irradiated from the probe 10 forms a focal point in a narrow region so as to correspond to a portion of the ROI, and beamforming of the echo signal received by the probe 10 is performed to form two to eight scan lines. Therefore, in comparison with the plane wave elasticity calculating scheme described above with reference to FIG. 4, the multi-beam elasticity calculating scheme described above with reference to FIG. 6 enables the second obtainment unit 240 to more accurately obtain elasticity information about the ROI.

The probe 10 repeats the above-described operation so as to obtain the echo signal for the whole ROI based on the control signal transmitted from the beamforming unit 210. In other words, the probe 10 may repeat an operation "irradiating the pushing beam->irradiating the ultrasound wave for forming a focal point at a portion of the ROI->receiving the echo signal->irradiating the pushing beam->irradiating the ultrasound wave for forming the focal point at the other portion of the ROI-> . . . ", thereby obtaining the echo signal for the whole ROI. The disclosure is not limited to the above-described operations, and additional operations may be repeated as necessary according to the number of portions of the ROI which are irradiated, until an echo signal is obtained for the whole ROI.

Referring again to FIG. 3, in operation 333, the second obtainment unit 240 obtains the second elasticity information. For example, the beamforming unit 210 performs the reception beamforming for the echo signal received by the probe 10, and transmits the beamformed signal to the second obtainment unit 240. The second obtainment unit 240 calculates a displacement of a shear wave by using the beamformed signal. The second obtainment unit 240 determines the second elasticity information by using the calculated displacement.

For example, the second obtainment unit 240 may determine a velocity of the shear wave inside the object 30, based on the calculated displacement. In this case, the second obtainment unit 240 may determine the velocity of the shear wave by using a wave equation, including the displacement of the shear wave as a variable, or an amount of change of the displacement of the shear wave based on time. A detailed method, in which the second obtainment unit 240 determines the velocity of the shear wave, is as described above with reference to operation 313.

Subsequently, the second obtainment unit 240 may determine the second elasticity information by using the determined velocity.

In operation 340, the third obtainment unit 250 obtains the third elasticity information of the ROI by using the first and second elasticity information. Here, the third elasticity information may include a value representing a strain, stiffness, Young's modulus, and/or shear modulus of each of the tissues composing the ROI. Hereinafter, a detailed method in which the third obtainment unit 250 obtains the third elasticity information of the ROI will be described with reference to FIG. 7.

Figure 7:
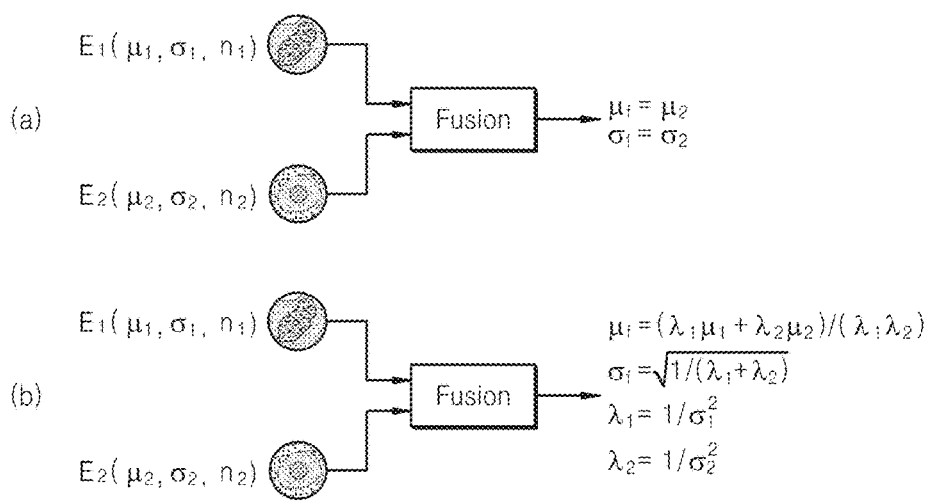
FIG. 7 includes diagrams for describing an example of an operation of a third obtainment unit according to an embodiment.

FIG. 7 is diagrams for describing an example of an operation of the third obtainment unit 250 according to an embodiment.

Referring to FIG. 7, the third obtainment unit 250 may obtain the third elasticity information in three schemes. However, in addition to the below-described three schemes, all schemes in which the third obtainment unit 250 combines the first and second elasticity information to obtain the third elasticity information may be used.

Hereinafter, for convenience of description, first elasticity values corresponding to an ROI among elasticity values included in the first elasticity information are assumed as E1 ($\mu1$, $\sigma1$, n1), and second elasticity values included in the second elasticity information are assumed as E2 ($\mu2$, $\sigma2$, n2). Here, $\mu$ denotes a mean value of a velocity of a shear wave in the ROI, and a denotes a standard deviation of the velocity of the shear wave in the ROI. Also, n1 denotes the number of pixels of a region corresponding to the ROI in an image which is generated based on the first elasticity information, and n2 denotes the number of pixels of an image which is generated based on the second elasticity information.

Referring to FIG. 7 (*a*), the third obtainment unit 250 may obtain the third elasticity information based on the second elasticity values. In other words, the third obtainment unit 250 obtains the third elasticity information by using the second elasticity values "E2 ($\mu2$, $\mu2$, n2)" among the first elasticity values "E1 ($\mu1$, $\sigma1$, n1)" and the second elasticity values "E2 ($\mu2$, $\sigma2$, n2)".

As described above with reference to FIG. 3, the second elasticity information may include more accurate elasticity information about the ROI than the first elasticity information. Therefore, the third obtainment unit 250 may obtain the third elasticity information based on the second elasticity information, thereby obtaining accurate elasticity information about the ROI.

Referring to FIG. 7 (*b*), the third obtainment unit 250 may obtain the third elasticity information by using the velocity "$\mu 1$" of the shear wave and the standard deviation "$\sigma 1$" of the velocity in the ROI among the first elasticity values, and the velocity "$\mu 2$" of the shear wave and the standard deviation "$\sigma 2$" of the velocity in the ROI among the second elasticity values.

First, the third obtainment unit 250 calculates a velocity "$\mu f$" of the shear wave and a standard deviation "$\sigma f$" of the velocity in the ROI by using the following Equation (3):

$$\mu_f = (\lambda_1 \mu_1 + \lambda_2 \mu_2)/(\lambda_1 + \lambda_2)$$

$$\sigma_f = \sqrt{1/(\lambda_1 + \lambda_2)} \quad (3)$$

where $\lambda_1$ and $\lambda_2$ may be calculated by using the following Equation (4):

$$\lambda_1 = 1/\sigma_1^2$$

$$\lambda_2 = 1/\sigma_2^2 \quad (4)$$

Subsequently, the third obtainment unit 250 obtains the third elasticity information by using the calculated velocity "$\mu f$" of the shear wave and the calculated standard deviation "$\sigma f$" of the velocity. Generally, it can be seen that the velocity "$\mu f$" of the shear wave may be calculated according to a first weight which is applied to the velocity "$\mu 1$" of the shear wave and a second weight which is applied to the velocity "$\mu 2$" of the shear wave. The first weight may be equal to zero and the second weight may be equal to one, as is the case in the scheme of FIG. 7(*a*). Or the first weight and the second weight may be greater than zero.

Referring again to FIG. 3, in operation 350, the image display apparatus 40 may display the first to third elasticity information. The first to third obtainment units 220, 240, and 250 respectively transmit the first to third elasticity information to the image display apparatus 40. The image display apparatus 40 may display the transmitted elasticity information.

FIG. 8 includes diagrams for describing an example in which an image display apparatus according to an embodiment displays the first to third elasticity information.

In FIG. 8, the total number of ROIs #1 to #3 is assumed as three. Also, each of first to third elasticity information is assumed as a shear modulus.

FIG. 8 (*a*) illustrates an example of each of first and second elasticity information about an ROI. For example, the image display apparatus 40 may display first elasticity information "Elasticity 1" and second elasticity information "Elasticity 2" about each of the ROIs #1 to #3. Here, each of the first elasticity information "Elasticity 1" and the second elasticity information "Elasticity 2" includes a mean value "Mean" and standard deviation "Std" of shear moduluses respectively corresponding to positions included in each ROI.

FIG. 8 (*b*) illustrates an example of third elasticity information about an ROI. For example, the image display apparatus 40 may display third elasticity information "Elasticity" about each of the ROIs #1 to #3. Here, the third elasticity information "Elasticity" includes a mean value "Mean" and standard deviation "Std" of shear moduluses respectively corresponding to positions included in each ROI. The illustrations in FIGS. 8(*a*) and 8(*b*) are merely examples. The information presented in FIGS. 8(*a*) and 8(*b*) may be separately displayed or combined and displayed together. All or some of the first to third elasticity information may be displayed at once. Additionally, or alternatively, all or some of the first to third elasticity information may be displayed in a text format, a graphical format, in color, or combinations thereof. Additionally, or alternatively, all or some of the first to third elasticity information may be displayed together with an elastography image (e.g., similar to that shown in FIG. 5). For example, all or some of the first to third elasticity information may be superimposed on the elastography image so that elasticity information may be overlaid on the elastography image (e.g., in a transparent manner).

Figure 9:
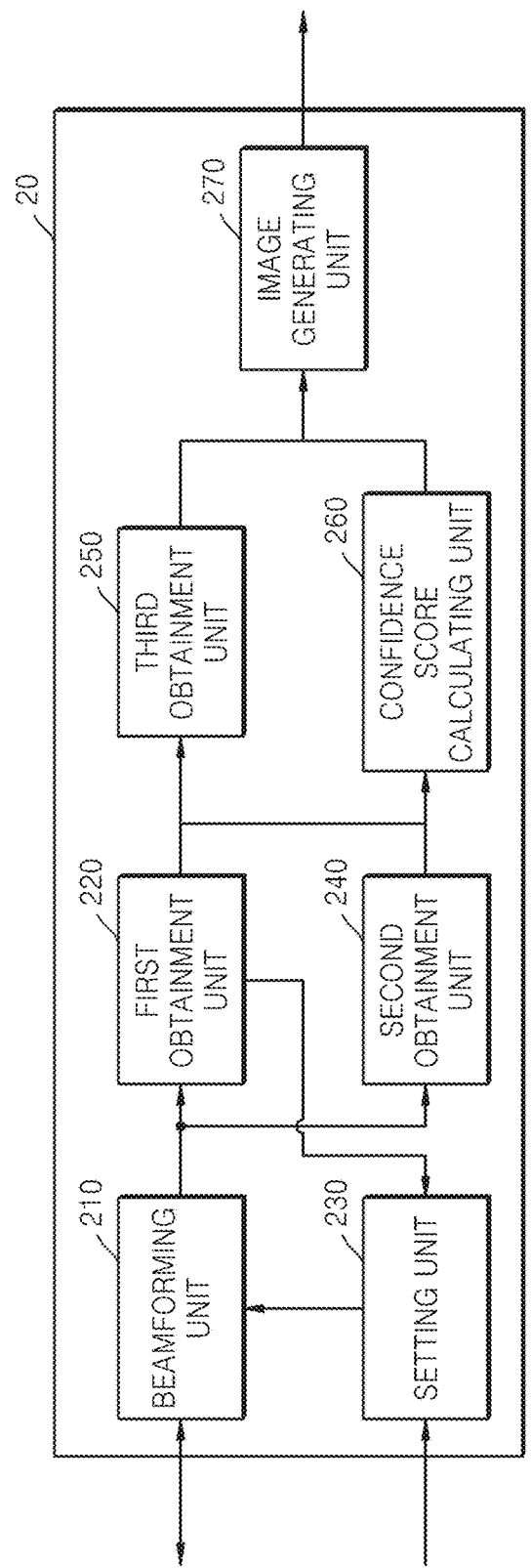
FIG. 9 is a block diagram of a shear wave processing apparatus according to another embodiment.

FIG. 9 is a block diagram of a shear wave processing apparatus 20 according to an embodiment.

Referring to FIG. 9, the shear wave processing apparatus 20 may include a beamforming unit 210, a first obtainment unit 220, a setting unit 230, a second obtainment unit 240, a third obtainment unit 250, a confidence score calculating unit 260, and an image generating unit 270.

The shear wave processing apparatus 20 of FIG. 9 is illustrated as including various elements associated with the shear wave processing apparatus 20. However, it will be understood by those of ordinary skill in the art that the shear wave processing apparatus 20 may further include general-use elements, in addition to the elements shown in FIG. 9.

Moreover, the beamforming unit 210, the first obtainment unit 220, the setting unit 230, the second obtainment unit 240, the third obtainment unit 250, the confidence score calculating unit 260, and the image generating unit 270 of the shear wave processing apparatus 20 of FIG. 9 may each correspond to one or more processors. Alternatively, one or more processors may correspond to one or more of the beamforming unit 210, the first obtainment unit 220, the setting unit 230, the second obtainment unit 240, the third obtainment unit 250, the confidence score calculating unit 260, and the image generating unit 270 of the shear wave processing apparatus 20 of FIG. 9. Each of the processors may be implemented as an array of a plurality of logic gates, or may be implemented as a combination of a general-use microprocessor and a memory that stores a program executable by the microprocessor. As another example, a processing device may be implemented using one or more general-purpose and/or special purpose computers, such as, for example, a processor, an image processor, a controller and an arithmetic logic unit, a central processing unit (CPU), a graphics processing unit (GPU), a digital signal processor (DSP), a microcomputer, a field programmable array, a programmable logic unit, an application-specific integrated circuit (ASIC), a microprocessor or any other device capable of responding to and executing instructions in a defined manner. Also, it will be understood by those of ordinary skill in the art that the elements may be implemented as another type of hardware.

Detailed operations of the beamforming unit 210, the first obtainment unit 220, the setting unit 230, the second obtainment unit 240, and the third obtainment unit 250 of the shear wave processing apparatus 20 are as described above with reference to FIGS. 2 to 8, and thus, their detailed descriptions are not repeated.

The confidence score calculating unit 260 may calculate confidence scores of elasticity values corresponding to an ROI among elasticity values included in first elasticity information and confidence scores of elasticity values included in second elasticity information.

The image generating unit 270 may generate elasticity information about the ROI by using generated first to third elasticity information. In addition, the first to third obtainment units 220, 240, and 250 may generate elasticity information by using the first to third elasticity information. In an embodiment, the shear wave processing apparatus 20 may not include the image generating unit 270.

Hereinafter, detailed operations respectively performed by the above-described elements included in the shear wave processing apparatus 20 will be described with reference to FIG. 10.

Figure 10:
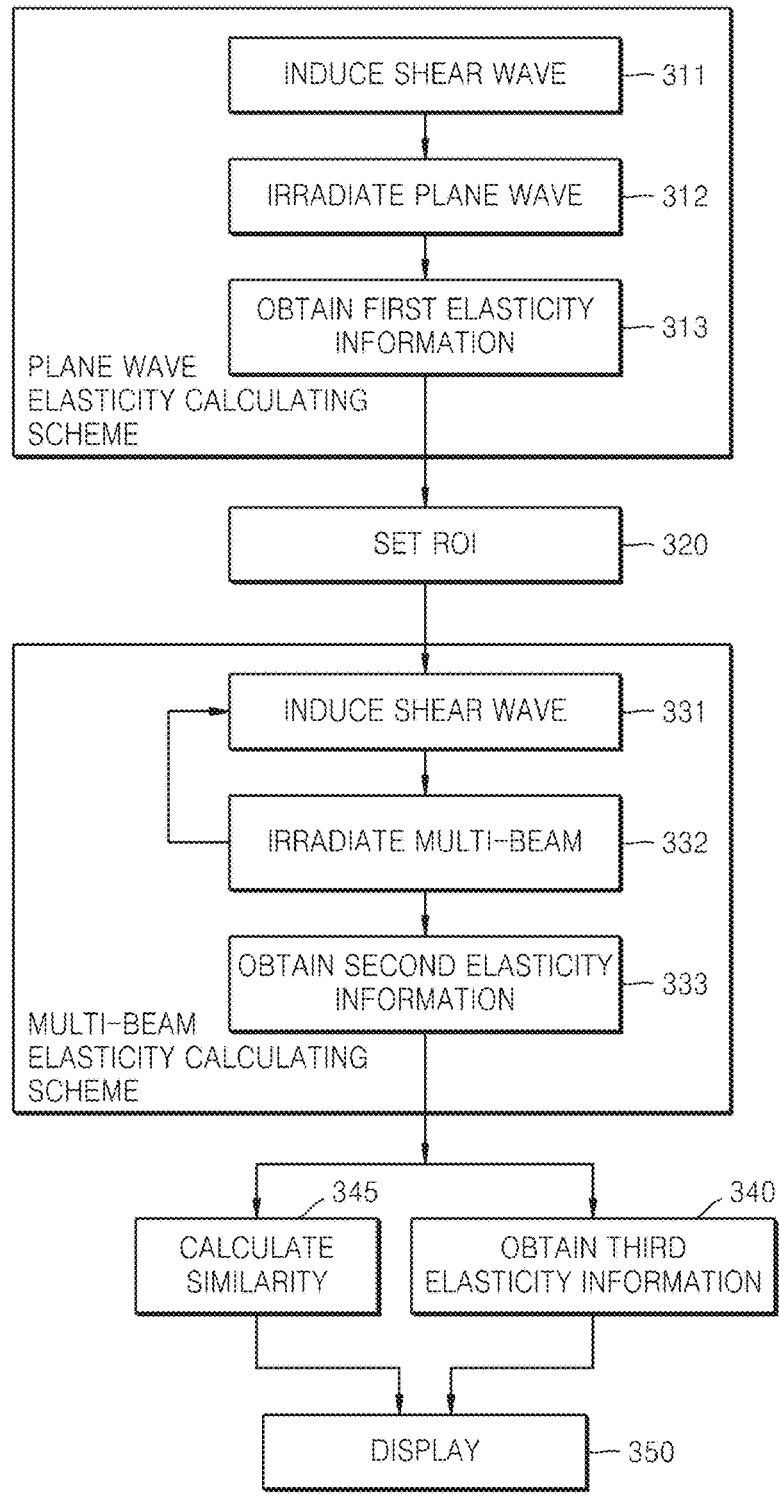
FIG. 10 is a flowchart for describing another example of an operation performed by the elasticity analysis system according to an embodiment.

FIG. 10 is a flowchart for describing an operation performed by the elasticity analysis system according to an embodiment.

Operations 311 to 340 of FIG. 10 are similar to those described above with reference to operations 311 to 340 of FIG. 3, and thus, their detailed descriptions are not repeated.

In operation 345, the confidence score calculating unit 260 calculates confidence scores of elasticity values corresponding to an ROI among elasticity values included in first elasticity information and confidence scores of elasticity values included in second elasticity information. Here, each of the confidence scores denotes a numerical value representing a similarity of the elasticity values corresponding to the ROI among the elasticity values included in the first elasticity information and the elasticity values included in the second elasticity information.

For example, the confidence score calculating unit 260 may perform a Student's t-test to calculate a confidence score. When the elasticity values corresponding to the ROI among the elasticity values included in the first elasticity information are assumed as E1 ($\mu1$, $\sigma1$, n1) and the elasticity values included in the second elasticity information are assumed as E2 ($\mu2$, $\sigma2$, n2), the confidence score calculating unit 260 may calculate an input value "t" necessary to perform the Student's t-test, by using the following Equation (5):

$$t = \frac{\mu_1 - \mu_2}{\sigma_{12}\sqrt{1/n_1 + 1/n_2}} \quad (5)$$

where $\mu$ denotes a mean value of a velocity of a shear wave in an ROI and $\sigma$ denotes a standard deviation of the velocity of the shear wave in the ROI. Also, $n_1$ denotes the number of pixels of a region corresponding to the ROI in an image which is generated based on the first elasticity information, and $n_2$ denotes the number of pixels of an image which is generated based on the second elasticity information.

Moreover, $\sigma_{12}$ of Equation (5) may be calculated by using the following Equation (6):

$$\sigma_{12} = \sqrt{\frac{(n_1-1)\sigma_1^2 + (n_2-1)\sigma_2^2}{n_1 + n_2 - 2}} \quad (6)$$

The confidence score calculating unit 260 may apply t, calculated from Equation (5), to the Student's t-distribution to calculate a confidence score. Here, the calculated confidence score denotes a numerical value representing a similarity of the elasticity values corresponding to the ROI among the elasticity values included in the first elasticity information and the elasticity values included in the second elasticity information. For example, when the calculated confidence score is assumed as 95%, the elasticity values corresponding to the ROI among the elasticity values included in the first elasticity information and the elasticity values included in the second elasticity information have a similarity therebetween corresponding to a probability of 95%.

In operation 350, the image display apparatus 40 may display the first to third elasticity information and the confidence score. For example, as described above with reference to FIG. 8 (b), when the image display apparatus 40 displays the third elasticity information, the image display apparatus 40 may display the confidence score along with the third elasticity information. The first to third elasticity information and the confidence score may be separately displayed or combined and displayed together. All or some of the first to third elasticity information and the confidence score may be displayed at once. Additionally, or alternatively, all or some of the first to third elasticity information and the confidence score may be displayed in a text format, a graphical format, in color, or combinations thereof.

Moreover, as described above with reference to FIG. 9, when the shear wave processing apparatus 20 further includes the image generating unit 270, the image display apparatus 40 may display an elastography image generated by the image generating unit 270. Additionally, or alternatively, all or some of the first to third elasticity information and the confidence score may be displayed together with the elastography image (e.g., similar to that shown in FIG. 5). For example, all or some of the first to third elasticity information and the confidence score may be superimposed on the elastography image so that elasticity information may be overlaid on the elastography image (e.g., in a transparent manner).

Figure 11:
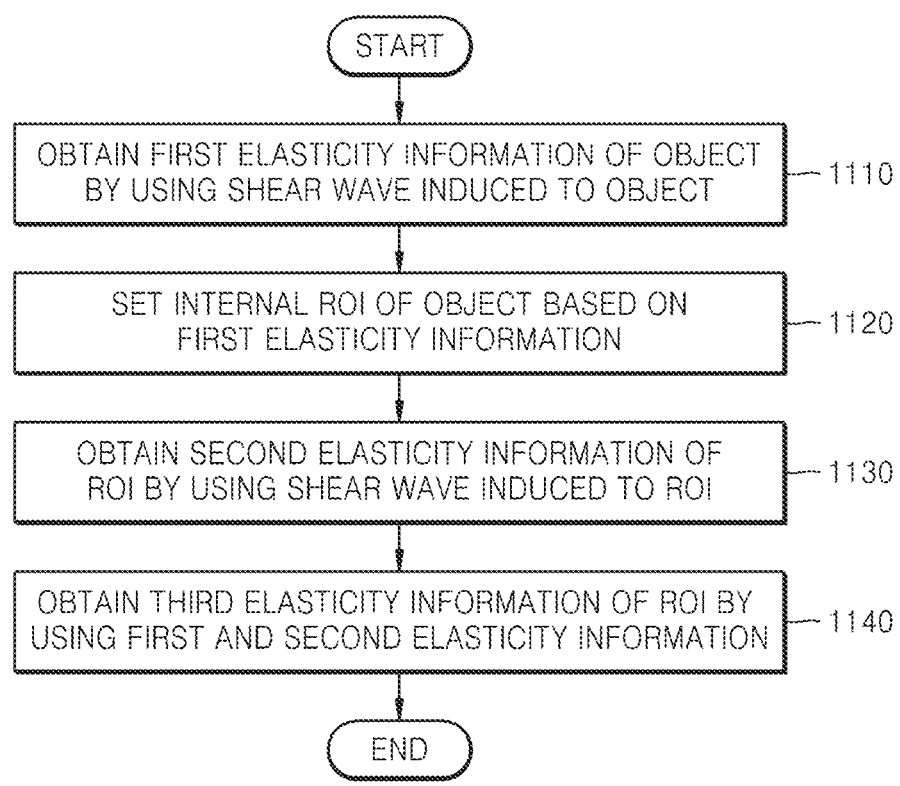
FIG. 11 is a flowchart of a method of obtaining elasticity information about an ROI, according to an embodiment.

FIG. 11 is a flowchart of a method of obtaining elasticity information about an ROI, according to an embodiment.

Referring to FIG. 11, the method of obtaining elasticity information about an ROI includes a plurality of operations that may be performed in a time series by the elasticity analysis system 1 or the shear wave processing apparatus 20 of FIGS. 1, 2, and 9. For example, the plurality of operations performed by the elasticity analysis system 1 or the shear wave processing apparatus 20 may be performed in a sequential manner. Thus, although not described below, the above-described details of the elasticity analysis system 1 or the shear wave processing apparatus 20 of FIGS. 1, 2, and 9 may be applied to the method of obtaining elasticity information about an ROI in FIG. 11.

In operation 1110, the first obtainment unit 220 obtains first elasticity information of an object by using a shear wave induced to the object.

In operation 1120, the setting unit 230 sets an internal ROI of the object based on the first elasticity information.

In operation 1130, the second obtainment unit 240 obtains second elasticity information of the ROI by using a shear wave induced to the ROI.

In operation 1140, the third obtainment unit 250 obtains third elasticity information of the ROI by using the first and second elasticity information.

As described above, according to the one or more of the above embodiments of the disclosure, the shear wave processing apparatus 20 obtains the third elasticity information by using the first and second elasticity information which are obtained by using the different processes, and thus accurately obtains the elasticity information (for example, the elasticity value and/or the elastography image) about the tissues composing the ROI.

The above-described method may be written as one or more computer programs and may be implemented in general-use digital computers that execute the programs including program instructions using a computer-readable recording medium. Data structures used in the above-described method may be recorded in a computer-readable recording medium by using various methods. Examples of the computer-readable recording medium include magnetic storage media (e.g., ROM, RAM, USB, flash memory, floppy disks, hard disks, etc.), storage media such as optical recording media (e.g., CD-ROMs or DVDs) and PC interfaces (e.g., PCI, PCI-express, Wi-Fi, etc.). Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Each block of the flowchart illustrations may represent a unit, module, segment, or portion of code, which comprises one or more executable instructions for implementing the specified logical function(s).

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the disclosure have been described with reference to the figures, it will be understood by those of ordinary skill in the art that various changes in form and details may be made therein without departing from the spirit and scope of the disclosure as defined by the following claims.

What is claimed is:

1. A method comprising:
    obtaining, by at least one processor, first elasticity information by transmitting a plane ultrasound wave to a tissue disposed in an area of an object on which a first shear wave is induced;
    setting, by the at least one processor, an internal region of interest (ROI) within the area of the object to a region of the tissue within the area of the object having the first elasticity information greater than a predetermined threshold value;
    obtaining, by the at least one processor, second elasticity information by transmitting an ultrasound wave that forms a focal point at a portion of the ROI on which a second shear wave is induced;
    combining, by the at least one processor, the first elasticity information and the second elasticity information;
    obtaining, by the at least one processor, third elasticity information of the ROI based on the combination of the first elasticity information and the second elasticity information; and
    generating, by the at least one processor, an elastography image with respect to the ROI, based on the third elasticity information.

2. The method of claim 1, wherein the obtaining of first elasticity information comprises:
    receiving an echo signal of the plane ultrasound wave which is transmitted to the object;
    performing beamforming of the echo signal, and calculating a displacement of the first shear wave induced to the object by using the beamformed signal; and
    determining a velocity of the first shear wave induced to the object by using the calculated displacement.

3. The method of claim 2, wherein the plane ultrasound wave comprises an ultrasound wave that does not form a focal point in a region corresponding to the object.

4. The method of claim 2, wherein the determining comprises determining the velocity of the first shear wave induced to the object by using a wave equation, including the displacement, or by using a change amount of the displacement based on time.

5. The method of claim 1, wherein the obtaining of second elasticity information comprises:
    receiving an echo signal of the ultrasound wave which is transmitted to the ROI;
    performing beamforming of the echo signal to form at least one or more scan lines, and calculating a displacement of the second shear wave induced to the ROI by using the beamformed signal; and
    determining a velocity of the second shear wave induced to the ROI by using the calculated displacement.

6. The method of claim 5, wherein the determining comprises determining the velocity of the second shear wave induced to the ROI by using a wave equation, including the displacement, or by using a change amount of the displacement based on time.

7. The method of claim 1, wherein the obtaining of third elasticity information comprises obtaining the third elasticity information by using a velocity of the first shear wave and a standard deviation of the velocity in the ROI among a plurality of elasticity values included in the first elasticity information and a velocity of the second shear wave and a standard deviation of the velocity in the ROI among a plurality of elasticity values included in the second elasticity information.

8. The method of claim 1, further comprising calculating confidence scores of elasticity values included in the first elasticity information and confidence scores of elasticity values included in the second elasticity information.

9. A non-transitory computer-readable storage medium which stores a program, that when executed, implements the method of claim 1.

10. An apparatus comprising:
    at least one memory configured to store instructions; and
    at least one processor configured to execute the stored instructions:
        to obtain first elasticity information by transmitting a plane ultrasound wave to a tissue disposed in an area of an object on which a first shear wave is induced,
        to set an internal region of interest (ROI) within the area of the object, based on the first elasticity information, by setting the internal ROI to a region of the tissue within the area of the object having the first elasticity information greater than a predetermined threshold value,
        to obtain second elasticity information by transmitting an ultrasound wave that forms a focal point at a portion of the ROI on which a second shear wave is induced,
        to combine the first elasticity information and the second elasticity information;

to obtain third elasticity information of the ROI based on the combination of the first elasticity information and the second elasticity information, and to generate an elastography image with respect to the ROI, based on the third elasticity information.

11. The apparatus of claim 10, wherein the at least one processor is further configured to perform beamforming for an echo signal of the plane ultrasound wave which is transmitted to the object, calculate a displacement of the first shear wave induced to the object by using the beamformed signal, and determine a velocity of the first shear wave induced to the object by using the calculated displacement.

12. The apparatus of claim 11, wherein the plane ultrasound wave comprises an ultrasound wave that does not form a focal point in a region corresponding to the object.

13. The apparatus of claim 10, wherein the at least one processor is further configured to perform beamforming for a received echo signal of the ultrasound wave which is transmitted to the ROI, to form at least one or more scan lines, calculate a displacement of the second shear wave induced to the ROI by using the beamformed signal, and determine a velocity of the second shear wave induced to the ROI by using the calculated displacement.

14. The apparatus of claim 10, wherein the at least one processor is further configured to obtain the third elasticity information by using a velocity of the first shear wave and a standard deviation of the velocity in the ROI among a plurality of elasticity values included in the first elasticity information and a velocity of the second shear wave and a standard deviation of the velocity in the ROI among a plurality of elasticity values included in the second elasticity information.

15. The apparatus of claim 10 wherein the at least one processor is further configured to calculate confidence scores of elasticity values included in the first elasticity information and confidence scores of elasticity values included in the second elasticity information.

* * * * *